United States Patent [19]

Elias et al.

[11] Patent Number: 5,324,300
[45] Date of Patent: Jun. 28, 1994

[54] DEVICE FOR THE CONTROLLED EXCISION OF TISSUE FROM A LIVING BODY

[76] Inventors: Elias G. Elias, 1214 Merediths Ford Rd., Towson, Md. 21204; Robert J. Chapolini, 9907 Forge Park Rd., Perry Hall, Md. 21128

[21] Appl. No.: 782,663

[22] Filed: Oct. 25, 1991

[51] Int. Cl.$^5$ .............................................. A61B 17/20
[52] U.S. Cl. .................................... 606/180; 606/179
[58] Field of Search ............... 606/180, 179, 170, 172, 606/173; 128/751-755

[56] References Cited

U.S. PATENT DOCUMENTS

| | | | |
|---|---|---|---|
| 493,730 | 3/1893 | MacKenzie | 606/179 |
| 4,142,517 | 3/1979 | Stavropoulos et al. | 606/179 |
| 4,306,570 | 12/1981 | Matthews | 606/179 |
| 4,461,305 | 7/1984 | Cibley | 606/180 |
| 4,576,162 | 3/1986 | McCorkle | 606/180 |
| 4,696,308 | 9/1987 | Meller et al. | 606/180 |
| 4,895,146 | 1/1990 | Draenert | 606/180 |
| 4,913,143 | 4/1990 | Oloff et al. | 606/179 |
| 5,040,542 | 8/1991 | Gray | 606/179 |
| 5,087,247 | 2/1992 | Horn et al. | 606/192 |

Primary Examiner—Edgar S. Burr
Assistant Examiner—Anthony H. Nguyen
Attorney, Agent, or Firm—Howard Califano

[57] ABSTRACT

A device to rapidly and safely excise tissue samples from a living body including a means to prevent lateral movement of the cutting edge as it engages the tissue and a means to control the depth of excision. The device also features an external sheath which is driven into the tissue with the coring shaft and which provides the operator with continued access to the sampling site after removal of the tissue core.

19 Claims, 8 Drawing Sheets

DEVICE FOR THE CONTROLLED EXCISION OF TISSUE FROM A LIVING BODY

BACKGROUND OF THE INVENTION

1. Field of the Invention

The invention relates to a device for the controlled excision of a piece of tissue from a living body. The term "tissue," as used herein, refers, but is not limited to dense structures such as bone and other calcified structures and to soft structures such as solid organs and tumors. The tissue removed could be for the purpose of diagnosing a suspected pathologic condition that is involving the tissue, and/or for the purpose of completely removing all diseased tissue, thus effecting treatment of the disease. Another purpose of removing a piece of tissue would be to provide an access port to fluid or tissue below the surface of an organ or structure; the aspiration of marrow from the cavity of a bone is an example of this application of the invention.

2. Description of Prior or Contemporary Art

In the practice of clinical and research medicine, the practitioner is frequently required to remove a piece of tissue from an organ or structure that is suspected to be involved with a disease process. The tissue is then sent for microscopic examination and/or culture so that a diagnosis of the exact pathologic process can be made. At times, the entire area of suspected involvement is removed so that the disease process is not only diagnosed but is also definitively treated. Excision of diseased tissue may be performed through a surgical incision; the tissue then is excised under direct vision. Alternatively, the tissue may be excised by an instrument that is passed through a puncture wound in the skin and directed to the area of interest. This percutaneous technique eliminates the recovery period required after an open procedure. This in turn reduces the costs of the procedure as well as morbidity.

Three essential conditions must be satisfied by a device used to excise tissue: 1) The device must be controllable so that it does not deviate from the area of interest during the cutting process; 2) The depth of penetration must be displayed to the operator or controlled by a mechanical stop so that underlying structures deep to the area of interest are not damaged; 3) The sample of tissue cannot be crushed or otherwise damaged by the excision process which could result in an inaccurate pathologic diagnosis. A forth condition, required in specific applications, is continued access to the area where tissue has be removed. This would allow removal of additional tissue either by further excision or by aspiration. It would also permit application of a plug in the void at the excision site, thereby preventing hemorrhage or leakage of other bodily fluids.

There have been many prior art devices developed to remove tissue from a living body, some used during a surgical operation, others used percutaneously. Many of these devices utilize a narrow gauge hollow needle which is plunged into the area of interest and then withdrawn; a very small core of tissue is thus harvested. There are many variations to the "plunge type" instruments, but since none use a moving cutting edge, there use is limited to very soft tissue. A potential problem with these devices is that the architecture of the excised tissue may not be preserved due to compression of the specimen, even when used in soft tissue. Also, the depth of the tissue core cannot be monitored effectively.

U.S. Pat. No. 4,262,676 describes a bone biopsy device developed by Jamshidi that uses a hollow shaft cutter which is manually driven into the tissue using an oscillating rotational motion. A significant amount of pressure has to be maintained on the instrument to advance into the bone; when performing a biopsy on an irregularly shaped bone, the device may deviate laterally, and possibly completely slip off the surface. This can result in damage to surrounding structures or, minimally, not excising tissue from the precise area of interest. The device can only be used to excise a core from relatively soft cancellous bone. It does not incorporate a depth control feature.

There have many prior art devices developed to provide a more controlled excision of a core of hard tissue such as bone, some of which use a powered cutting cylinder. U.S. Pat. No. 4,306,570 describes a device used to excise hard tissue which features two counterrotating concentric cutting edges that are said to eliminate the problem of lateral migration as the cutting edges engage the tissue. The device neither has a depth control feature nor a means to allow for continued access to the area of excision after the core of tissue has been removed.

U.S. Pat. No. 3,893,445 describes a device for the biopsy of bone marrow which consists of a sheath device and a central cutting needle. The sheath is first positioned on the surface of the bone; a cutting cannula is then introduced through the sheath to excise a core of bone. The sheath does not substantially penetrate the bone and, therefore, one must maintain its position manually throughout the procedure in order to provide continued access to the tissue following removal of a core sample. No depth control feature is provided in this device.

U.S. Pat. No. 4,142,517 describes another instrument which uses a sheath that minimally penetrates the bone surface to prevent lateral deviation of a cutting shaft which is subsequently introduced. After the core is excised, the sheath may be driven into the bone as a separate operation, thus giving the operator continued access to the underlying tissue.

SUMMARY OF THE INVENTION

The present invention provides a means of excising a core of tissue from a living body in a safe and controlled manner either percutaneously or during a surgical operation. The core of tissue is not altered by the excision method, thereby allowing for accurate examination and diagnosis. The device can be positioned to a specific area to be excised and, by virtue of a lateral control means, this position can be maintained as the cutting edge engages the tissue surface. The chance of the device slipping off the surface of the tissue to be excised and damaging adjacent structure is greatly reduced compared to prior art devices.

The depth of tissue core to be excised is displayed to the operator and, if desired, can be pre-set so that a predetermined depth cannot be exceeded. This design feature makes the procedure safer, as underlying structures deep to the area to be excised would not be injured.

The present invention also, if desired, provides for continued access to the site of excision after the core of tissue has been removed. This is effected by incorporating an external, penetrating sheath which is temporarily affixed to or embedded into the tissue surface. The operator does not have to manually hold the sheath in position after it is placed, thereby freeing up both hands for the remainder of the procedure. Placement of the penetrating sheath occurs as the core of tissue is excised, thereby eliminating additional steps in the procedure.

The sheath is especially useful when the operator desires to asperate fluid from the void left in the tissue (e.g. in the case of bone marrow aspiration) or excise additional tissue adjacent or deep to the previous core. Additionally, the clinician may wish to place a plug in the void remaining in the tissue after specimen excision in order to prevent the escape of fluid. It would be impossible to percutaneously locate the area of excision after removal of the cutting cylinder without an external sheath which remains attached to the tissue surface. To maintain the position of a non-penetrating or minimally penetrating, manually held sheath is difficult after removing the central cutting cylinder.

A first novel feature of the invention is the use of a hollow cutting shaft with a lateral location means that prevents deviation of the device thereby allowing for retrieval of a tissue specimen from a specific location.

A second novel feature is the use of a lateral location means that does not substantially alter the structure of the excised tissue specimen, thereby allowing for precise microscopic examination.

A third novel feature of the invention is the use of an external sheath that is affixed to the tissue and which may be temporarily left in place, thereby providing the operator with continued access to the exact area of excision for further removal of tissue, aspiration of fluid, and/or placement of a plug to seal the hole created by the procedure.

A forth novel feature of the invention is the use of an external sheath that is affixed to the surrounding tissue simultaneously with penetration by a central coring cylinder thus lessening the number of individual steps in the procedure.

A fifth novel feature of the invention is to provide access to fluid contained within a solid structure by first removing a plug of tissue with the cutter shaft, then aspirating the fluid through a sheath affixed to the structure.

A sixth novel feature of the invention is the use of the movement of a slidable central guide pin as a means to monitor the depth of core excision in addition to providing a means of lateral location of the cutting cylinder.

A seventh novel feature of the invention is the use of the contact of a slidable central guide pin with a mechanical stop to prevent excision of a core of tissue beyond a pre-set depth.

An eighth novel feature of the invention is the improved safety that results from the prevention of lateral movement of the cutting shaft over the surface of the tissue and possible damage to adjacent structures.

A ninth novel feature of the invention is the positive control over the depth of core excised, thereby preventing possible damage to structures that lay deep to the area.

A tenth novel feature of the invention is the elimination of operator technique as a factor in excising tissue, thereby producing specimens that are more consistent.

The above-mentioned features, as well as other features of the present invention, all become readily apparent from the following non-limiting description and the accompanying drawings.

SUMMARY OF THE DRAWINGS

The above-enumerated objects and features of the present invention will more fully appear from the following detailed description when read in conjunction with the accompanying drawings. It is to be understood that the drawings are for the purpose of illustration only and are not intended as a definition of the limits of the invention.

BRIEF DESCRIPTION OF PREFERRED EMBODIMENTS

Figure 1:
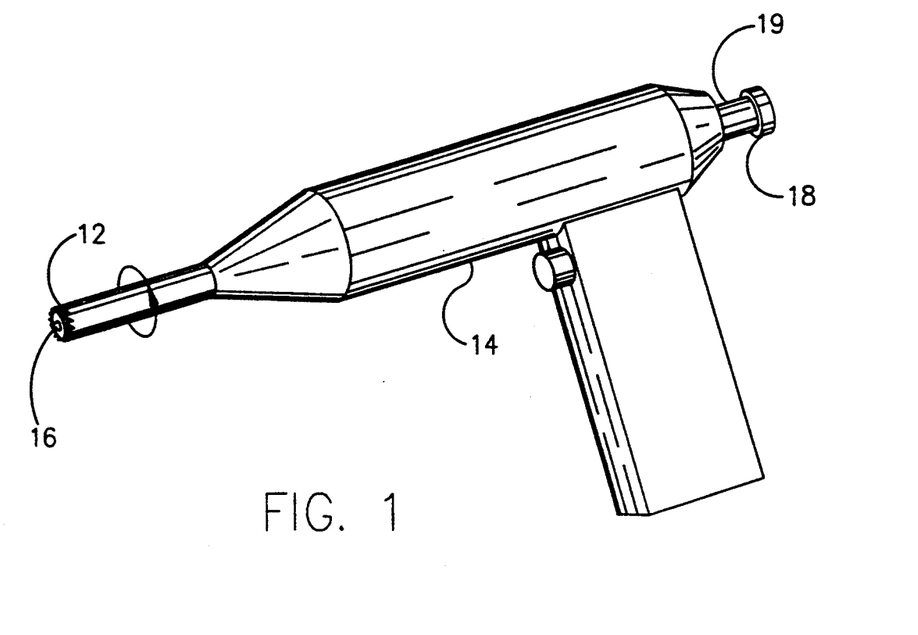
FIG. 1 is a view of an embodiment of the tissue coring device with central guide pin locked in place.

In FIG. 1, a preferred embodiment of the invention is shown. The hollow cutting shaft 10 with its saw tooth cutting edge 12 is driven by a power unit 14. Although this particular embodiment uses rotational motion applied to the cutting edge, it should be understood that other embodiments of the invention could employ an oscillating motion or a percussive force to propel the cutting edge. It should also be understood that different cutting edges may be employed, including smooth and serrated, depending on the nature of the tissue to be excised.

The distal end of the central guide pin 16 is shown in the locked position with its tip protruding just beyond the cutting edge 12. The proximal tip of the guide pin 18 employs a simple threaded coupling to secure itself to the proximal end of the cutting shaft 19. This allows the tip of the guide pin 16 to be firmly pressed against the surface when a linear force is applied through the cutting shaft 10.

Figure 2:
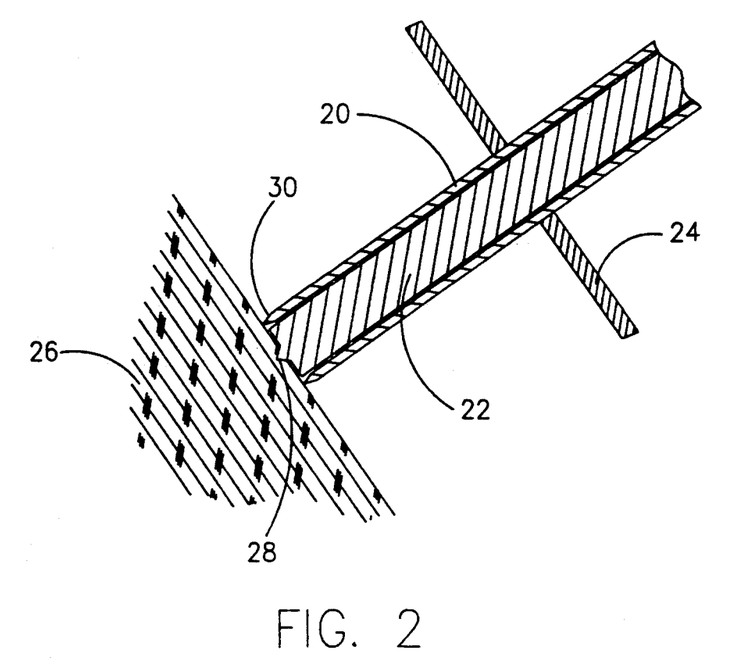
FIG. 2 is a cross sectional view of the distal end of the device being used for percutaneous tissue excision, the tip of the guide pin seen slightly impressed into the tissue surface.

FIG. 2 is a cross sectional view of the invention being used percutaneously to excise a core of tissue. The cutting shaft 20, with its guide pin 22 locked in place, has been introduced through the skin 24 and placed against the tissue 26. The protruding tip 28 at the distal end of guide pin 22 is shown having been impressed into the surface of the tissue 26. The illustrated embodiment of the guide pin 22 has a single pointed protrusion 28, although alternate embodiments may have several protrusions, a protrusion that is threaded like a self-tapping screw, a drill bit protrusion, or other methods of gaining purchase of the tissue to be cored.

The guide pin tip 28 may be impressed into the tissue 26 by a separate percussive or linear force or rotational motion applied to the guide pin 22. Alternatively, the guide pin tip 28 may be driven into the tissue 26 by the force which is used to propel the cutting shaft 20 into the tissue 26, this force being transmitted from the cutting shaft 20 to the guide pin 22 through a coupling. Other embodiments of the central guide pin may use non-penetrating means to affix itself to the tissue surface, such as a vacuum applied through an orifice in its distal end. In any case, the tip of the guide pin 28 must penetrate or affix itself to the surface of the tissue 26 or adherent structure covering the tissue before the cutting edge 30 engages these tissues, thus preventing any lateral deviation of the cutting edge 30 from the exact location to be cored.

In the preferred embodiment of the invention, the depth of penetration of the guide pin tip 28 is very shallow so as not to significantly alter the structure of the core to be excised. In this case it is necessary to maintain some linear force transmitted from the cutting shaft 20 to the guide pin tip 28 through a guide pin 22-cutting shaft 20 coupling as the coring procedure commences. The linear force along the guide pin 22 is released when the cutting edge 30 firmly engages the tissue 26.

Figure 3:
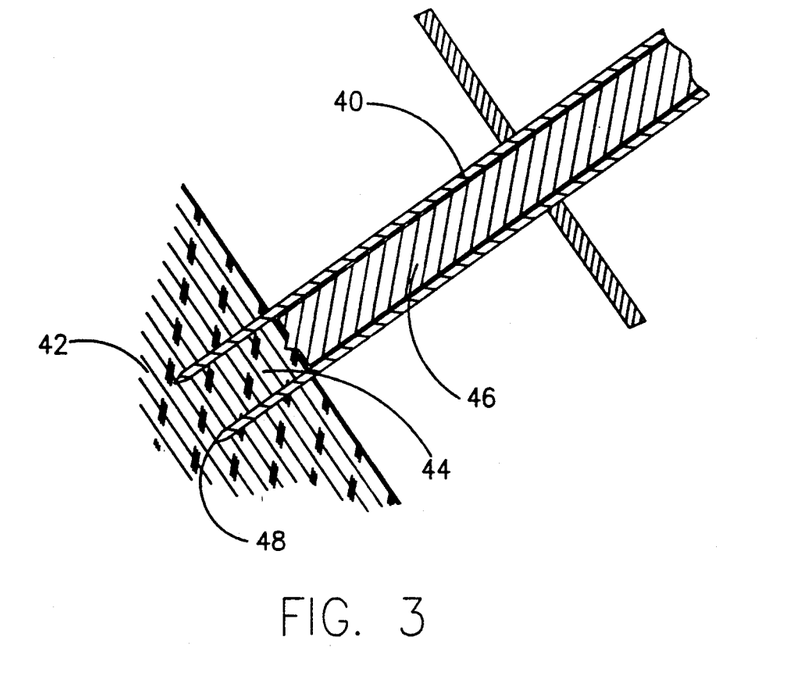
FIG. 3 is a cross sectional view of the distal end of the device penetrating a tissue structure by using a rotational motion applied to the cutting edge, the central guide pin seen freely sliding through the cutting shaft so as not to further penetrate the core of tissue.

FIG. 3 is a cross sectional view of the cutting shaft-guide pin combination. The cutting shaft 40 is penetrating the tissue 42 by a rotational movement, producing a core of tissue 44 inside the cutting shaft 40. The guide pin 46 slidably moves within the cutting shaft 40 as the core 44 is taken, thus damage to the specimen by further penetration of the guide pin 46 is prevented. When the desired depth of core has been reached, the core 44 is snapped free of the surrounding tissue 42 by applying a gentle side-to-side motion of the cutting shaft 40. The device is then withdrawn with the core of tissue being retained in the cutting shaft 40.

Figure 4:
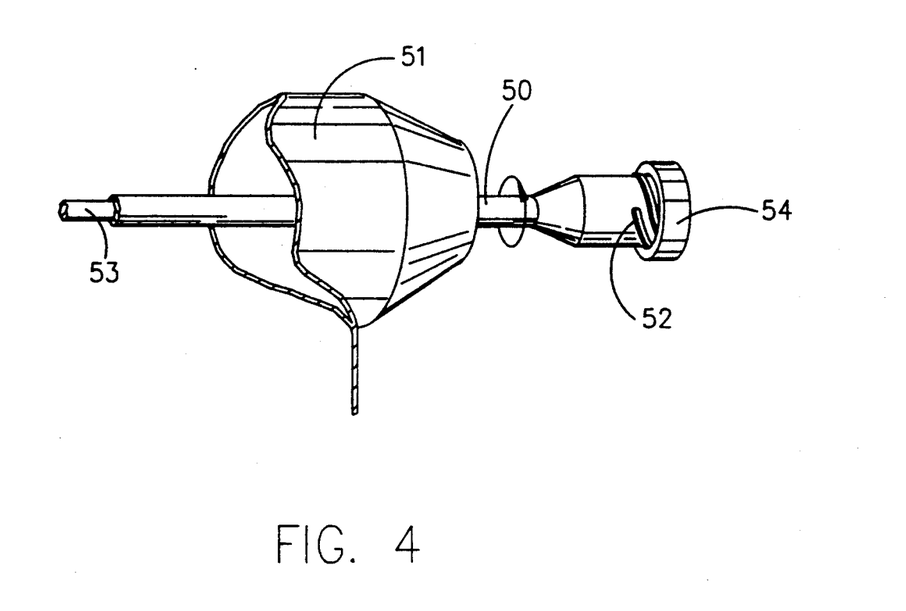
FIG. 4 is an enlarged view of the proximal end of the coring device detailing one embodiment of a self releasing connection between the cutting shaft and the central guide pin, shown in this figure as the two begin to uncouple.

In FIG. 4 an embodiment of the coupling between the proximal end of the cutting shaft 50 and the proximal end of the guide pin is illustrated. This particular embodiment employs a threaded coupling between a male fitting 52 which is rigidly attached to the cutting shaft 50 and a female fitting 54 which is rigidly attached to the guide pin 53. The proximal end of the drive unit 51 is also illustrated. As the cutting shaft 50 rotates and begins to core into the tissue, its rotational velocity becomes greater than that of the guide pin 53, thus unlocking the threaded coupling between the cutting shaft fitting 52 and the guide pin fitting 54.

Figure 5:
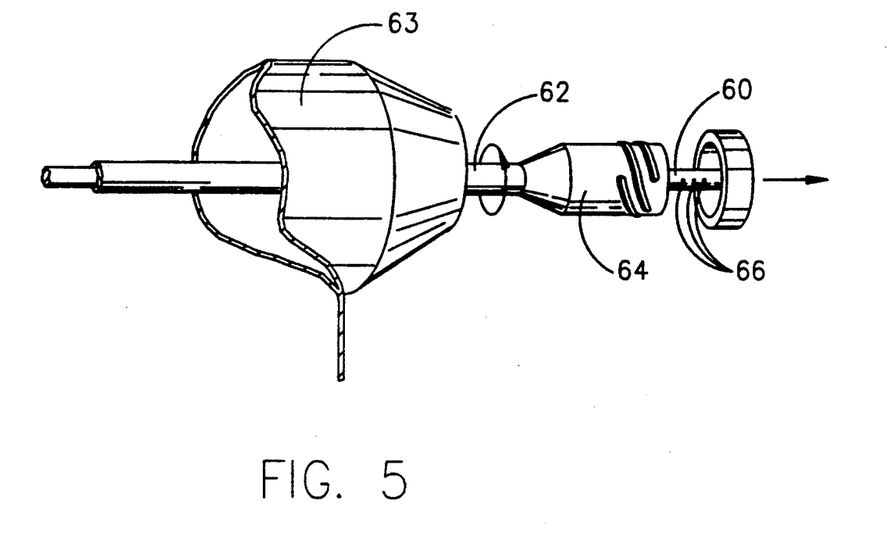
FIG. 5 details the same embodiment of the self releasing connection shown in FIG. 4 after the two elements become uncoupled, the central locating pin seen to be moving distal with respect to the cutting shaft as the core is taken.

FIG. 5 illustrates the relative movement of the guide pin 60 in relation to the cutting shaft 62 and its rigidly attached fitting 64. Index markings 66 on the guide pin 60 show the operator exactly how deep the cutting shaft 62 has penetrated the tissue.

Other embodiments of a coupling between the guide pin and the cutting shaft may be employed to allow for the two to release as the core is taken, so that no additional penetration of the specimen by the guide pin takes place. It should also be understood that a guide pin may be used that is driven into specimen for a sufficient distance that no cutting shaft-guide pin coupling is necessary to maintain contact between the tip of the guide pin and the surface of the tissue to be cored. Such a guide pin would freely slide through the cutting shaft during all phases of the coring operation.

Figure 6:
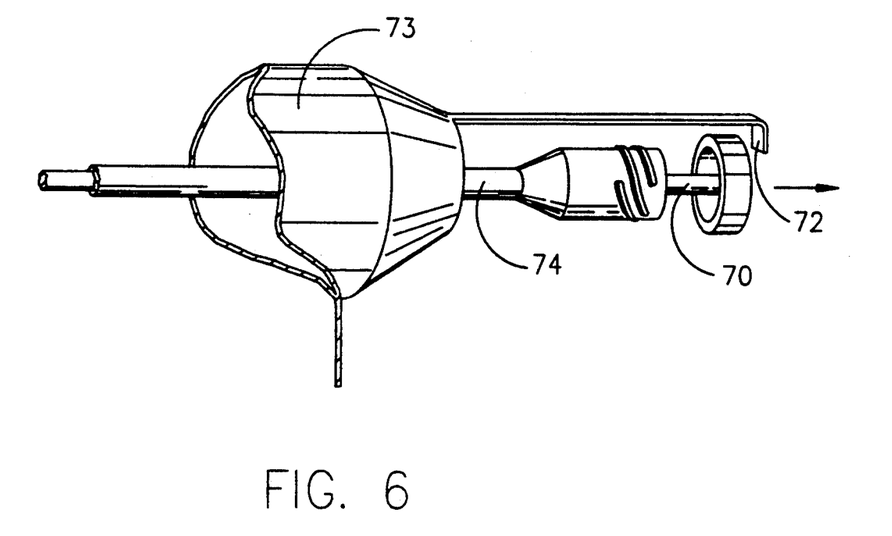
FIG. 6 illustrates use of the central locating pin as a means for positive control of depth of the core specimen.

FIG. 6 illustrates the use of the sliding central guide pin 70 and a stationary mechanical stop 72 attached to the proximal end of the drive unit 73 as a positive depth control mechanism. During the coring process, the guide pin 70 will move with respect to the cutting shaft 74 until it contacts the mechanical stop 72. The operator is thus prevented from taking a core beyond the pre-set depth.

Alternate embodiments of the positive depth control feature may be used including ones that are fully adjustable. The operator would set the depth before taking the core of tissue.

Figure 7:
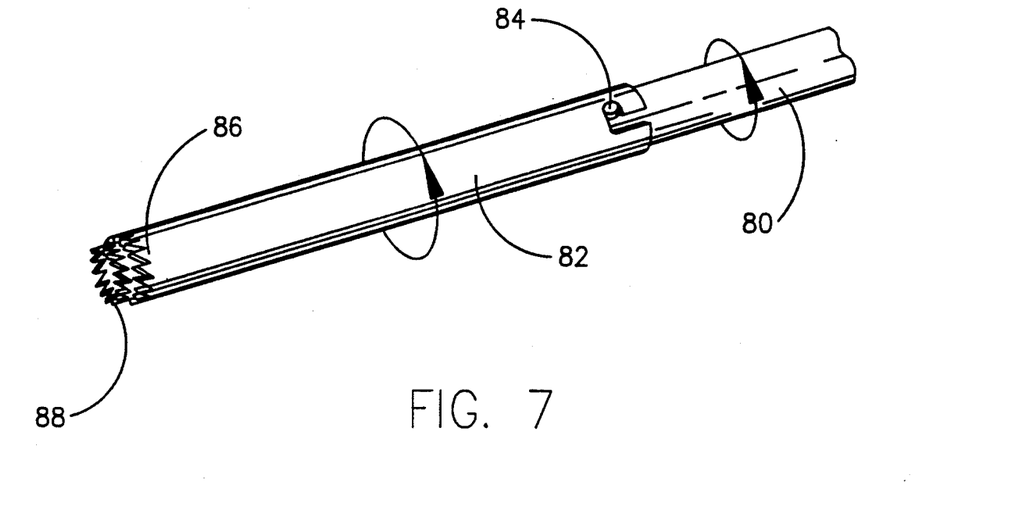
FIG. 7 is a view of the sheath-cutter embodiment of the invention.

FIG. 7 illustrates the sheath-cutting shaft embodiment of the invention. The cutting shaft 80 and the sheath 82 are rotated together, the rotational motion being transmitted from the cutting shaft 80 to the sheath 82 through the drive pin 84. The sheath-cutting shaft combination are unlocked by rotating the cutting shaft 80 opposite to the illustrated cutting direction; the cutting shaft 80 may then be withdrawn from the sheath 82. In this embodiment, the cutting teeth of the cutting shaft 88 lay distal to the teeth of the sheath 86. For purposes of clarity, the central guide pin is not shown.

Figure 8:
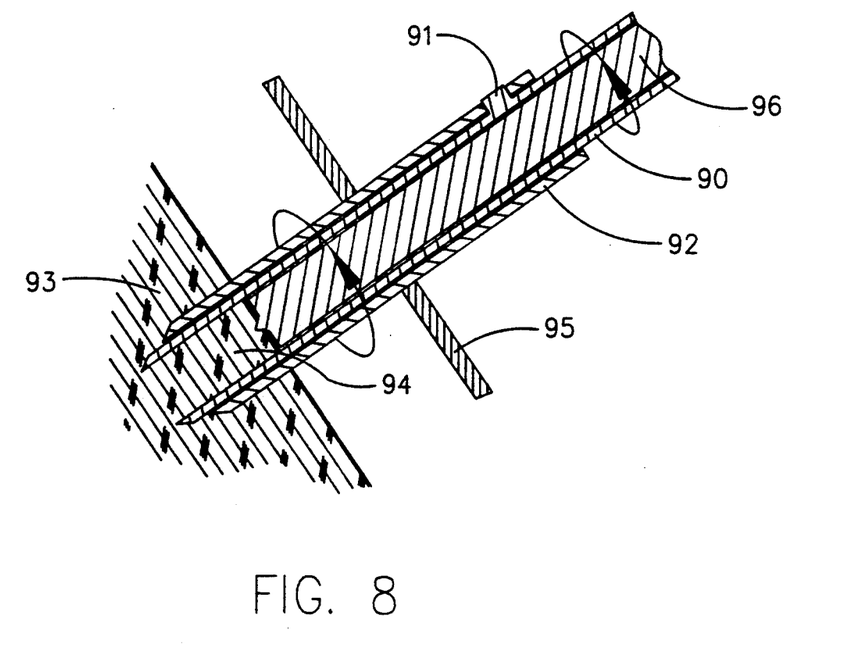
FIG. 8 is a cross sectional view of the sheath-cutter embodiment of the invention, the two simultaneously being rotationally driven into the tissue.

FIG. 8 is a cross sectional view of the sheath-cutting shaft embodiment as the two are being driven into tissue 93 through a puncture in the skin 95. The rotational motion is being supplied to the sheath 92 by the cutting shaft 90 through the drive pin 91. A core of tissue 94 has displaced the guide pin 96 proximally with respect to the cutting shaft 90.

Figure 9:
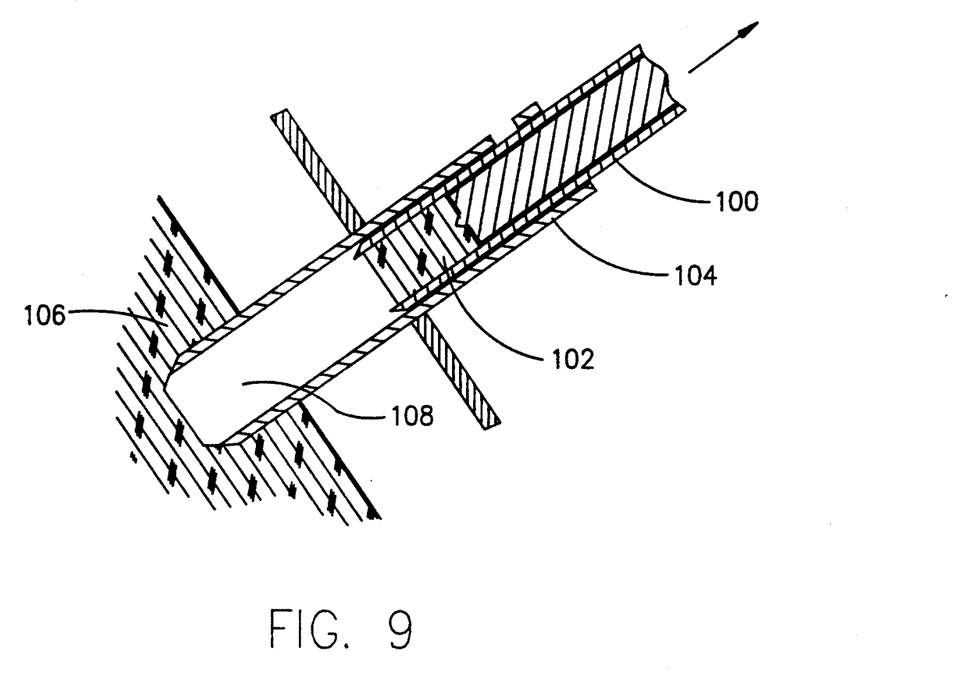
FIG. 9 illustrates the embedded external sheath in FIG. 8 after removal of the central cutter with its core of tissue, the sheath thus giving continued access to the void in the tissue.

In FIG. 9 the coring motion has been halted and the cutting shaft 100 with its core of tissue 102 is being slidably withdrawn after having been unlocked from the sheath 104. The sheath 104, which remains firmly embedded in the surrounding tissue 106, allows for continued access to the resulting tissue cavity 108. Fluid may be aspirated or injected through the sheath 104, and/or additional tissue may be subsequently excised deep to the previous specimen. At the end of the procedure, the sheath 104 allows for placement of a hemostatic agent or other type of material to plug the cavity 108, thereby preventing escape of fluid from the tissue 106. The sheath 104 also can be used as way of implanting a tissue dwelling device, either acutely or chronically. When access to the site is no longer needed, the sheath 104 is removed from the surrounding tissue 106 by applying a rocking or twisting motion to it while simultaneously pulling on its proximal end.

Figure 10:
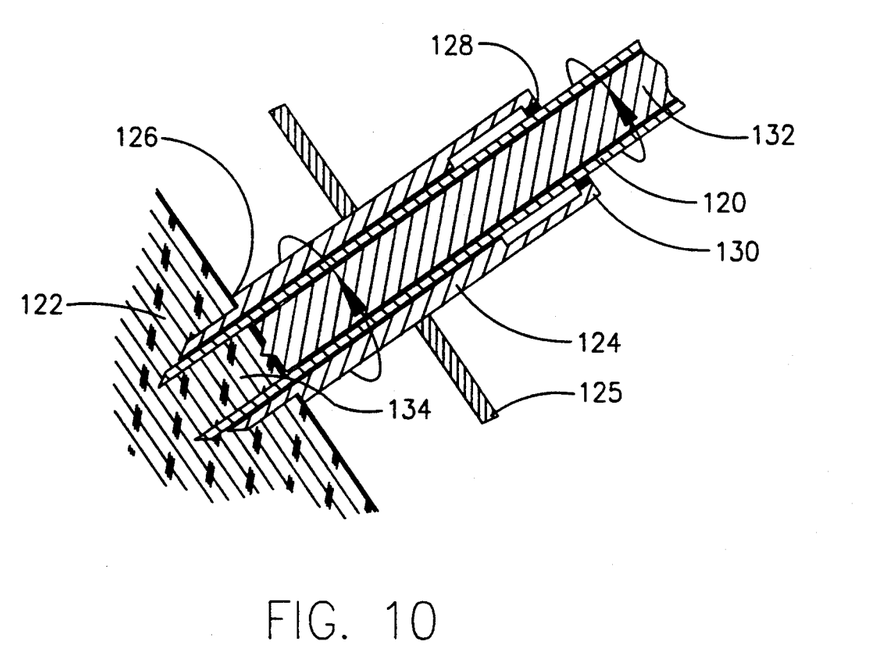
FIG. 10 is an alternate embodiment of the sheath-cutter design in cross section, the sheath being driven with the rotating cutting shaft through a friction coupling until the sheath's penetration is halted by a step fashioned in its outside diameter, the central cutting shaft continuing into the depths of the tissue for an additional distance.

FIG. 10 illustrates another embodiment of the sheath-cutting shaft combination, in cross section. The combination is introduced through the skin 125 to perform a percutaneous excision of tissue 122. In this illustration, the sheath 124 is being driven into the tissue 122 using the rotational motion from the cutting shaft 120 through a friction coupling consisting of several protrusions on the cutting shaft 128 in contact with protrusions on the sheath 130. As the step 126 in the sheath 124 makes contact with the surface of the tissue structure 122, the friction coupling between the cutting shaft 120 and the sheath 124 releases, stopping progression of the sheath 124 while allowing for continued forward advancement of the cutting shaft 120. The guide pin 132 is slidably moving up the cutter shaft 120 as the core 134 is taken.

Figure 11:
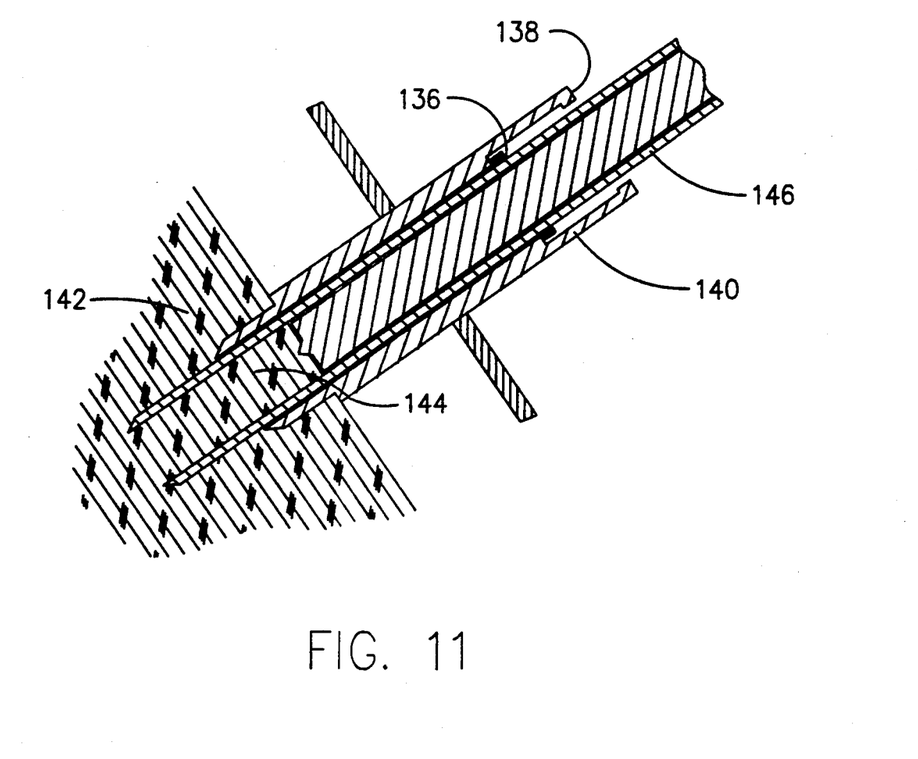
FIG. 11 illustrates the sheath-cutter embodiment shown in FIG. 10 with the cutting shaft's distal end having penetrated the tissue for a distance beyond the distal end of the sheath.

In FIG. 11, the friction coupling has released and the cutting shaft 146 has been driven deep into tissue 142, producing a core 144. After the desired depth of core has been reached, the operator gently rocks the cutting shaft 146 from side to side to break the core 144 free from the surrounding tissue 142. The cutting shaft 146 with its tissue core 144 is then withdrawn, leaving the sheath 140 embedded in the tissue 142.

Figure 12:
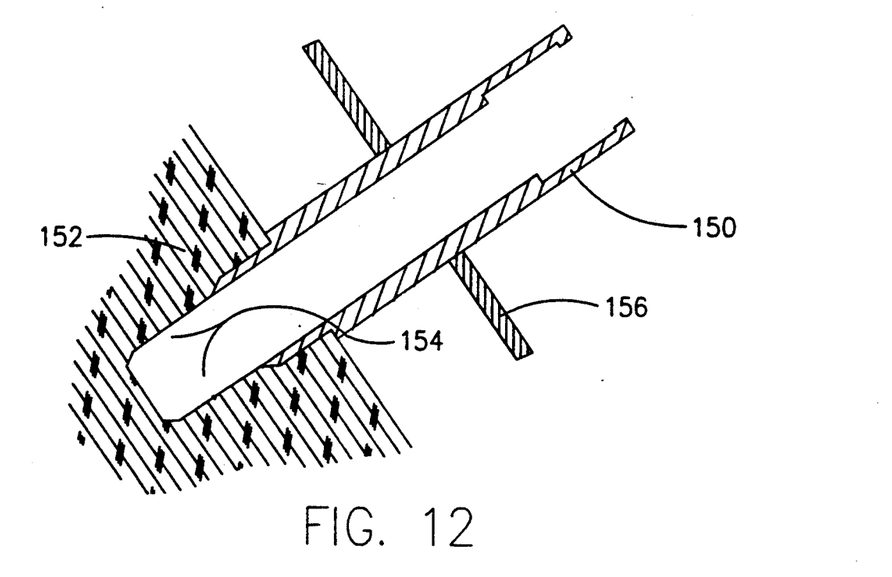
FIG. 12 illustrates the external sheath remaining embedded in the tissue after removal of the cutting shaft with its core of tissue, thus giving access to a large surface area inside the cavity remaining.

In FIG. 12, the cutter shaft and its core have been removed, leaving the sheath 150 firmly embedded in tissue 152. The sheath 150 gives access to the large surface area 154 of the cavity after the core is removed. Without the sheath 150, re-establishing contact with the cavity 154 through the skin 156 would be very difficult. The sheath 150 is easily removed from the tissue 152 at the end of the procedure.

Figure 13:
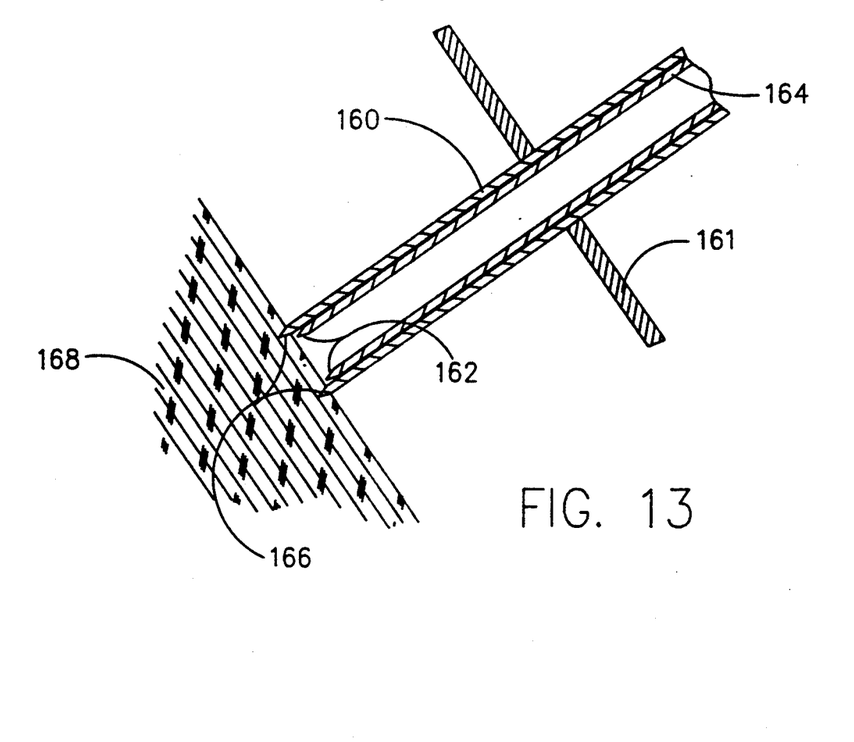
FIG. 13 shows an alternate embodiment of the invention where a penetrating sheath provides both lateral location of the cutting edge and for continued access to the cavity, shown in this illustration with the distal end of the sheath embedded into the tissue surface before contact is made by a centrally placed cutting shaft.

FIG. 13 illustrates another embodiment of the invention where an external sheath 160 directed percutaneously through the skin 161 serves both as a means to prevent lateral deviation of the cutting edge 162 of a centrally placed cutting shaft 164 and as a means to provide access to the resulting tissue cavity after removal of a tissue core. The distal end 166 of the sheath 160 is first embedded into the tissue 168 or removably affixed to the tissue 168 before the cutting edge 162 engages the surface of tissue 168. Placement of the sheath may be done by needle or guide wire direction, as is commonly done in clinical percutaneous procedures.

Figure 14:
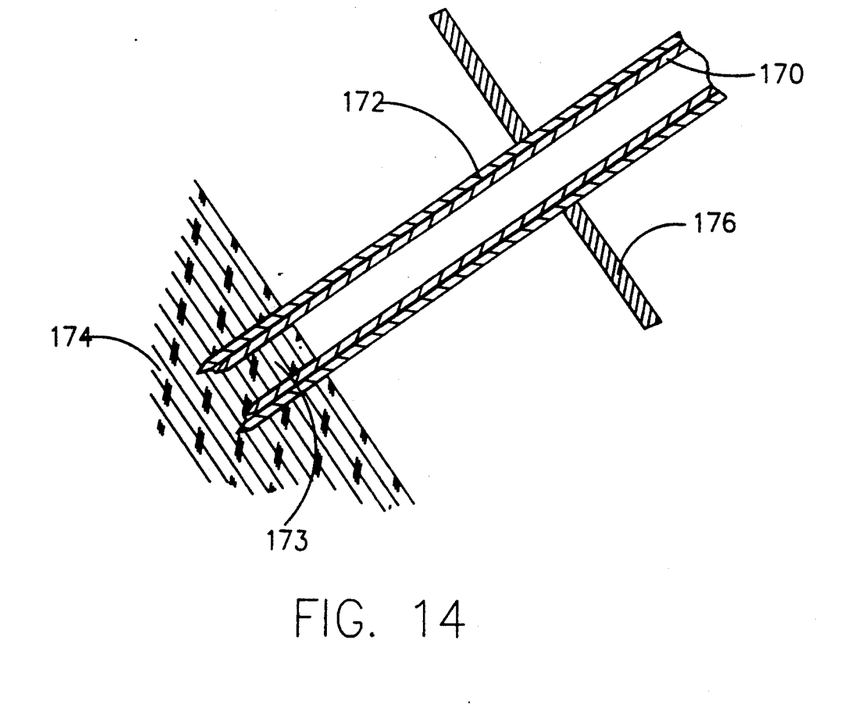
FIG. 14 is the embodiment in FIG. 13 with the central cutting shaft having propelled both itself and the external sheath into the tissue depths, thus giving continued access to the void in the tissue after removal of the cutting shaft with its tissue core.

In FIG. 14, the central cutting shaft 170 has been driven into the tissue 174 producing a tissue core 173. In this embodiment, the external sheath 172 is further driven into the tissue 174 by the coring action of the cutting shaft 170. The method of coupling the cutting shaft 170 and the sheath 172 could be similar to that illustrated in FIG. 7, or by the method shown in FIG. 10 if a partially driven sheath is desired. After removal of the cutting shaft 170 with its tissue core 173 the sheath 172 provides continued access to the cavity created by removing tissue core 173. At the end of the procedure, the sheath 172 is withdrawn through the skin 176.

Figure 15:
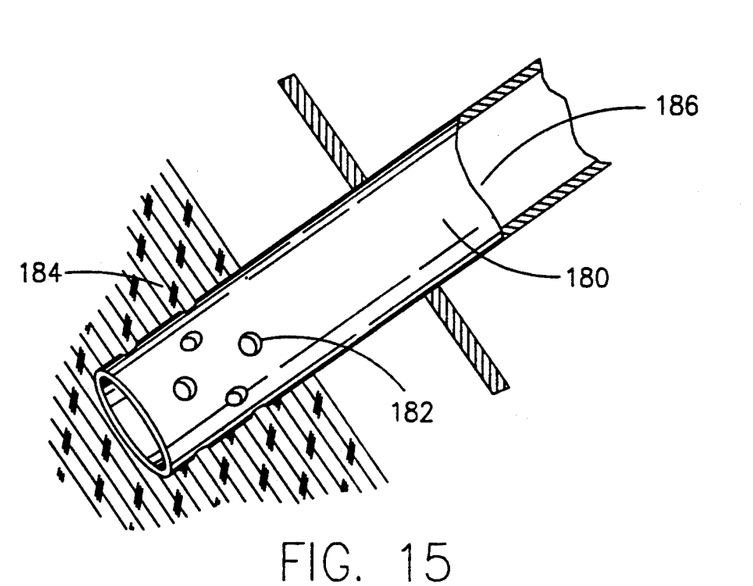
FIG. 15 is the distal aspect of an alternate embodiment of the sheath incorporating perforations which allow communication between the lumen and the outside of the sheath, thus giving access to additional surface area to the tissue surrounding it.

FIG. 15 illustrates an alternate embodiment of the sheath 180 where perforations 182 in the distal aspect allow communication between the lumen 186 and the outside tissue 184. This embodiment is especially useful when one wishes to aspirate or inject through the sheath 180; the perforations 182 allow for access to a greater surface area of the tissue 184 in which it is embedded, compared to the other embodiments of the sheath.

What is claimed:

1. A device for the excision of tissue from a living body, said device comprising:
    an elongated hollow cutting shaft, having an open distal end with having a cutting edge and an open proximal end, said hollow cutting shaft adapted to be propelled into said tissue thereby producing a core of tissue, said hollow cutting shaft adapted to be withdrawn from said living body with said excised core of tissue;
    a guide pin having a sharpened pencil tip on its distal end, said guide pin adapted to be slidably mounted through the proximal end of said hollow cutting shaft, the length of said guide pin being such that, when coupled to said hollow cutting shaft, the distal aspect of said guide pin protrudes beyond the cutting edge of said hollow cutting shaft thereby allowing for said guide pin to gain purchase of tissue before engagement of tissue by said hollow cutting shaft's cutting edge;
    a coupling mechanism comprising a male threaded fitting rigidly attached to the proximal end of said hollow cutting shaft and a female threaded fitting rigidly attached to the proximal end of said guide pin, said coupling mechanism allowing for a linear force applied to said cutting shaft to be transmitted to said guide pin; and,
    a driving means for applying a rotational motion to said hollow cutting shaft and to said guide pin, the direction of rotation causing the female guide pin fitting and the female hollow cutting shaft fitting to disengage as the relative speed of said guide pin becomes less than the speed of said hollow cutting shaft as said guide pin engages said tissue.

2. The device of claim 1, further comprising:
    an outer sheath having a distal cutting edge and an inner lumen to slidably receive said hollow cutting shaft, said sheath adapted to be driven into said tissue with said hollow cutting shaft, said outer sheath providing for continued access to the void left in said tissue after removal of said hollow cutting shaft with said tissue core; and
    a coupling means for mechanically coupling said hollow cutting shaft and said outer sheath means, said coupling means comprising at least one projection extending from the outer diameter of said hollow cutting shaft and engaging at least one slot in the proximal aspect of said outer sheath, said coupling means adapted to allow both longitudinal forces and rotational motion applied to the hollow cutting shaft to be transmitted to said outer sheath, said coupling means adapted to be subsequently manually disengaged to allow removal of said hollow cutting shaft.

3. The device of claim of 1, further comprising:
a means to limit the depth of coring of said hollow cutting shaft, said means comprising a mechanical stop affixed to the proximal portion of said driving means, and adapted to prevent the central guide pin from slidably moving in a proximal direction within said hollow cutting shaft beyond the position of said mechanical stop.

4. The device of claim 2 wherein the outside diameter of the distal most end of said outer sheath is less than the outside diameter of the adjacent proximal portion of said outer sheath, thereby forming a step on the outside surface of said outer sheath, said step contacting the tissue surface as the hollow cutting shaft and the outer sheath are propelled into said tissue, thereby preventing further penetration of said tissue.

5. The device of claim of 2 wherein said outer sheath has at least one hole adapted to provide communication between the inner lumen of said outer sheath and said tissue, external to said outer sheath.

6. A device for the excision of tissue from a living body, said device comprises:
a center guide pin, the distal end of said guide pin having a means for gaining purchase of tissue;
a hollow cutting cylinder slidably mounted over said guide pin for axial movement relative to said guide pin, said hollow cutting cylinder having a distal cutting edge;
a means for rotating the hollow cutting cylinder; and,
a coupling means for rotationally coupling said center guide pin to said hollow cutting cylinder for causing said guide pin to rotate with said cutting cylinder and fixing relative linear displacement so that the guide pin protrudes beyond the cutting edge of said hollow cutting cylinder and means to release said coupling means so that said cutting cylinder rotates about said guide pin and can extend axially.

7. The device of claim 6, wherein said coupling means is a means for selectively locking and releasing rotational and linear coupling between said guide pin and said hollow cutting cylinder.

8. The device of claim 6, wherein said coupling means is a manually operable means for selectively locking and releasing rotational and linear coupling between said guide pin and said hollow cutting cylinder.

9. The device of claim 6, wherein said means for purchasing tissue has a first distal means for engaging tissue and a second means for preventing further penetration.

10. The device of claim 7, wherein said means for gaining purchase is at least one tip protruding from a second flattened region wherein said at least one tip is adapted to gain purchase of tissue but is stopped from penetrating further into tissue by said flattened region.

11. The device of claim 7, wherein said means for gaining purchase is a tapered pencil point tip, the depth of penetration being impeded by increasing diameter of said tapered pencil point.

12. The device of claim 6, further including a means for monitoring relative linear displacement between the guide pin and the hollow cutting cylinder.

13. The device of claim 6, wherein said coupling means comprises a means for coupling said guide pin to said hollow cutting cylinder and for disengaging such coupling when the rotational speed of said guide pin becomes less than the rotational speed of said hollow cutting cylinder.

14. The device of claim 6, wherein said coupling means has a male threaded fitting rigidly attached to the proximal end of said hollow cutting cylinder and a female threaded fitting rigidly attached to the proximal end of said guide pin, whereby the direction of rotation of said hollow cutting cylinder causes said guide pin to disengage from said hollow cutting cylinder when the rotation speed of the guide pin becomes less than the rotational speed of said hollow cutting cylinder.

15. The device of claim 13, wherein said means for gaining purchase has a first distal means for engaging tissue and a second means for preventing further penetration.

16. The device of claim 13, wherein said means for gaining purchase is a tapered pencil tip.

17. A device for the excision of tissue from a living body, said device comprises:
a center guide pin, the distal end of said guide pin having a means for gaining purchase of tissue;
a hollow cutting cylinder slidably mounted over said guide pin for axial movement relative to said guide pin, said hollow cutting cylinder having a distal cutting edge;
a means for rotating the hollow cutting cylinder; and,
a coupling means for rotationally coupling said center guide pin to said hollow cutting cylinder and for fixing relative linear displacement so that the guide pin protrudes beyond the cutting edge of said hollow cutting cylinder, said coupling means including means for releasing such coupling when the rotational speed of said center guide pin becomes less relative to the rotational speed of said hollow cutting cylinder.

18. The device of claim 17, wherein said means for gaining purchase is at least one tip protruding from a flattened region wherein said at least one tip is adapted to gain purchase of tissue but is stopped from penetrating further into tissue by said flattened region.

19. The device of claim 17, wherein said means for gaining purchase is a tapered pencil point tip, the depth of penetration being impeded by increasing diameter of said tapered pencil point.

* * * * *